United States Patent
Davis

(10) Patent No.: US 7,898,424 B2
(45) Date of Patent: Mar. 1, 2011

(54) CENTRALIZED PATIENT MONITORING SYSTEM WITH DIRECTED AUDIO ALERTING

(75) Inventor: Carl Claude Davis, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 296 days.

(21) Appl. No.: 12/102,432

(22) Filed: Apr. 14, 2008

(65) Prior Publication Data

US 2009/0256709 A1    Oct. 15, 2009

(51) Int. Cl.
*G08B 23/00* (2006.01)

(52) U.S. Cl. .................. 340/573.1; 340/502; 600/300; 600/584

(58) Field of Classification Search ............... 340/573.1, 340/525, 524, 517, 501, 573.4, 540, 502; 600/300, 481, 508–509, 523–524, 584
See application file for complete search history.

(56) References Cited

U.S. PATENT DOCUMENTS

| | | | |
|---|---|---|---|
| 5,859,915 A * | 1/1999 | Norris | 381/75 |
| 6,778,672 B2 | 8/2004 | Breed et al. | |
| 6,893,396 B2 * | 5/2005 | Schulze et al. | 600/300 |
| 7,301,451 B2 * | 11/2007 | Hastings | 340/539.12 |
| 7,359,861 B2 * | 4/2008 | Lee | 704/277 |
| 2003/0023146 A1 * | 1/2003 | Shusterman | 600/300 |

OTHER PUBLICATIONS

American Technology Corporation, Product Lines/HSS; http://www.atcsd.com/site/content/view/34/47.
http://www.holosonics.com/?g&gclid=CK3N4ZLM5owCFQGPWAodr0t-6g.

* cited by examiner

*Primary Examiner* — Daniel Previl
(74) *Attorney, Agent, or Firm* — Adrus, Sceales, Strarke & Sawall, LLP

(57) ABSTRACT

A centralized patient monitoring system configured to enable each of a plurality of technicians to generally simultaneously monitor multiple patients is disclosed herein. The centralized patient monitoring system includes a computer adapted to receive patient data from the monitored patients, and a display configured to visually convey the patient data. The centralized patient monitoring system also includes a directional speaker configured to selectively generate a localized alarm in order to audibly alert one of the technicians when a monitored patient requires attention in a manner that is generally imperceptible to the other technicians.

11 Claims, 2 Drawing Sheets

CENTRALIZED PATIENT MONITORING SYSTEM WITH DIRECTED AUDIO ALERTING

BACKGROUND OF THE INVENTION

The subject matter disclosed herein relates to a centralized patient monitoring system with directed audio alerting.

Centralized patient monitoring systems enable a plurality of technicians to collectively monitor a large number of patients from a single location. In some applications, each technician can monitor as many as 96 patients. The centralized patient monitoring systems commonly implement audible alarms to identify patients that require immediate attention. When an alarm sounds, the appropriate technician may contact a caregiver in order to assist the identified patient.

One problem with conventional centralized patient monitoring systems is that each alarm is generally heard by all the technicians. Such systems can create a noisy and confusing environment, and can potentially desensitize the technicians to the sound of the alarm.

BRIEF DESCRIPTION OF THE INVENTION

The above-mentioned shortcomings, disadvantages and problems are addressed herein which will be understood by reading and understanding the following specification.

In an embodiment, a centralized patient monitoring system configured to enable each of a plurality of technicians to generally simultaneously monitor multiple patients includes a computer adapted to receive patient data from the monitored patients. The centralized patient monitoring system also includes a display configured to visually convey the patient data, and a directional speaker configured to selectively generate a localized alarm in order to audibly alert one of the technicians when a monitored patient requires attention in a manner that is generally imperceptible to the other technicians.

In another embodiment, a centralized patient monitoring system configured to enable each of a plurality of technicians to generally simultaneously monitor multiple patients includes a computer adapted to receive patient data from a plurality of monitored patients, and to analyze the patient data in order to identify any of the monitored patients that require attention. The centralized patient monitoring system also includes a display configured to visually convey the patient data, and a directional speaker configured to selectively to generate a localized alarm in response to the patient data analysis. The localized alarm comprises a narrow beam of audible sound waves directed at one of the plurality of technicians.

In another embodiment, a method for enabling each of a plurality of technicians to generally simultaneously monitor multiple patients includes collecting patient data from a plurality of monitored patients, and implementing a computer to analyze the patient data. The method also includes implementing a directional speaker to selectively generate a localized alarm in response to the patient data analysis. The localized alarm comprises a narrow beam of audible sound waves. The method also includes directing the narrow beam of audible sound waves at one of the technicians such that the technician can be audibly alerted in a manner that is generally imperceptible to the remaining technicians.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
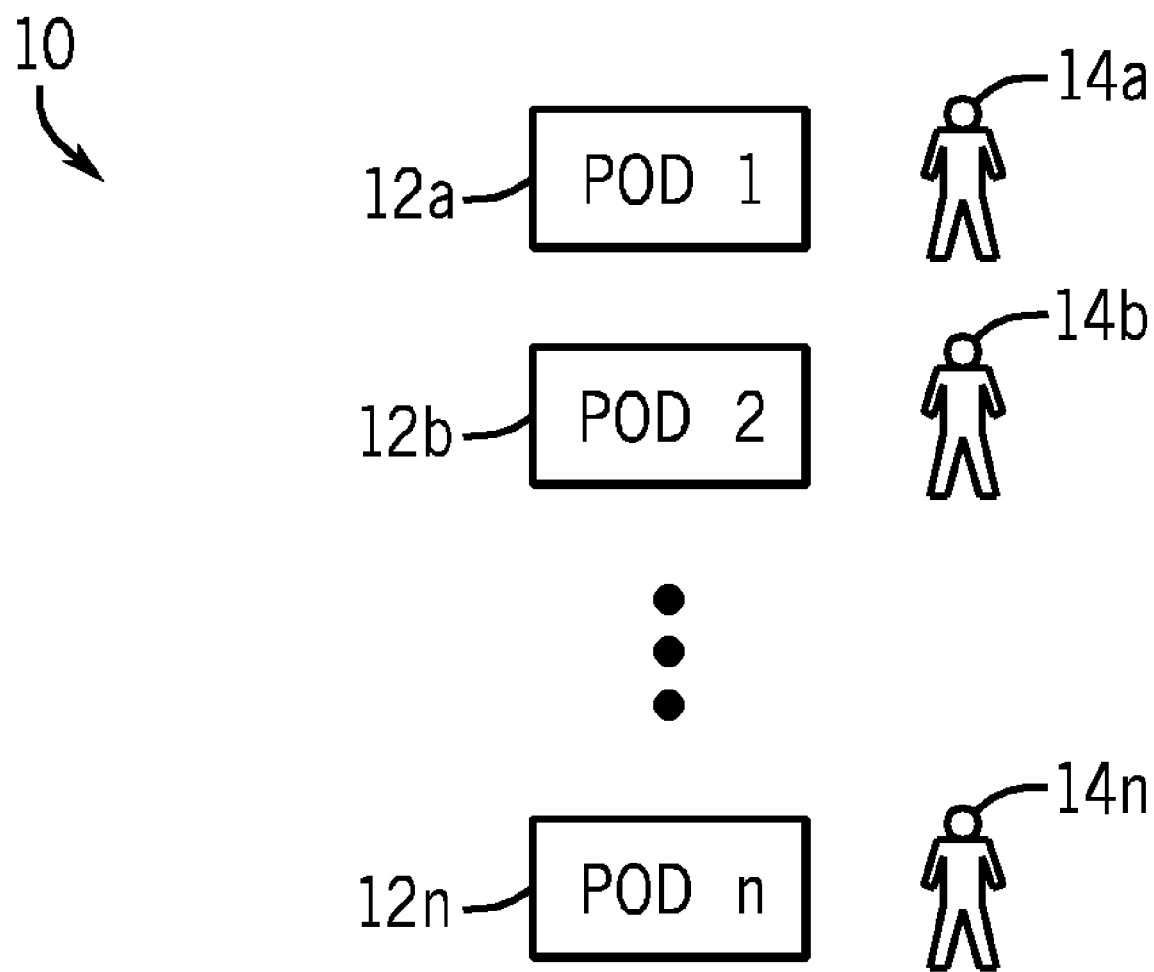
FIG. 1 is a schematic representation of a centralized patient monitoring system in accordance with an embodiment.

Referring to FIG. 1, a centralized patient monitoring system 10 is shown in accordance with one embodiment. The centralized patient monitoring system 10 includes a plurality of surveillance pods 12a-12n adapted to enable a corresponding plurality of technicians 14a-14n to monitor a large number of patients (not shown). It should be appreciated that the surveillance pods 12a-12n are similarly configured such that the following disclosure pertaining to surveillance pod 12a applies equally to the remaining surveillance pods 12b-12n.

Figure 2:
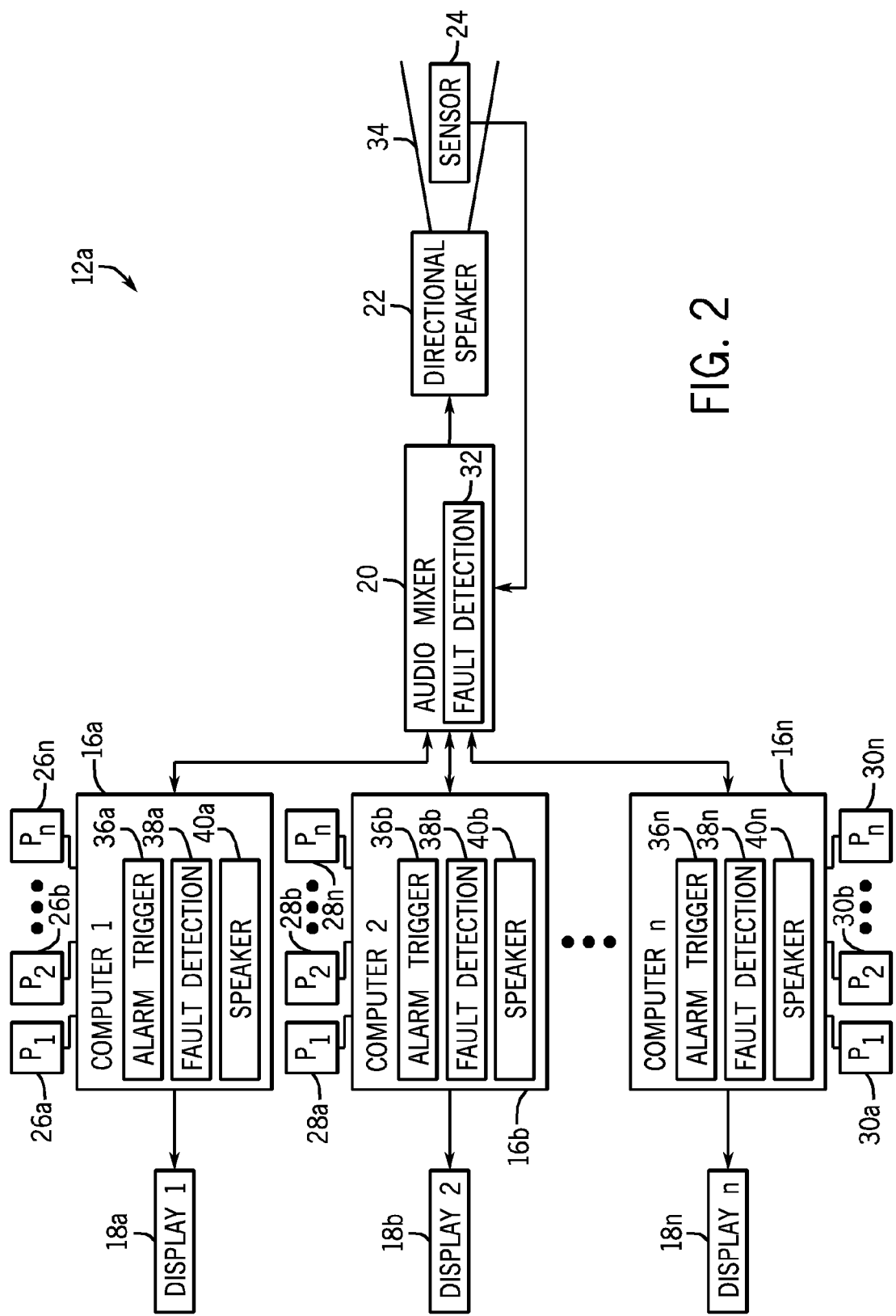
FIG. 2 is a schematic representation of one surveillance pod of the centralized patient monitoring system of FIG. 1 in accordance with an embodiment.

Referring to FIG. 2, the surveillance pod 12a is shown in accordance with one embodiment. The surveillance pod 12a includes a plurality of computers 16a-16n, a plurality of displays 18a-18n, an audio mixer 20, a directional speaker 22, and an audio sensor 24. Directional speaker technology is well known to those skilled in the art and will therefore not be described in detail.

The computer 16a is connected to a first plurality of discrete patient monitoring systems 26a-26n, the computer 16b is connected to a second plurality of discrete patient monitoring systems 28a-28n, and the computer 16n is connected to a $n^{th}$ plurality of discrete patient monitoring systems 30a-30n. The discrete patient monitoring systems 26a-26n, 28a-28n and 30a-30n are each configured to monitor an individual patient (not shown), to generate patient data based on the specific characteristics being monitored, and to transmit the patient data to one of the computers 16a-16. In a non-limiting manner, the discrete patient monitoring systems 26a-26n, 28a-28n and 30a-30n may each comprise an electrocardiograph, a blood pressure monitor, a thermometer, and/or a pulse oximeter. Correspondingly, the patient data generated by the patient monitoring systems 26a-26n, 28a-28n and 30a-30n may comprise electrocardiogram (ECG) data, blood pressure data, temperature data, and/or pulse data.

The computers 16a-16n are respectively connected to the displays 18a-18n. The displays 18a-18n are each configured to receive patient data from a respective computer 16a-16n, and to visually convey the patient data to the technician 14a (shown in FIG. 1). According to one embodiment, each of the displays 18a-18n is partitioned into 16 distinct regions that are each adapted to visually convey a different set of patient data such that the technician 14a can generally simultaneously monitor 16 different patients with a single display. According to another embodiment, one large monitor could be implemented in place of the individual monitors 18a-18n.

The computers 16a-16n are also connected to the audio mixer 20. The computers 16a-16n are each configured to selectively transmit an individual alarm signal to the audio mixer 20 as will be described in detail hereinafter. The audio mixer 20 is configured to receive the individual alarm signals from the computers 16a-16n, to combine the individual alarm signals into a single composite alarm signal, and to transmit the composite alarm signal to the directional speaker 22.

The audio mixer 20 may optionally include a fault detection algorithm 32 adapted to assess the operational status of the directional speaker 22. If the fault detection algorithm 32 determines that the directional speaker 22 is not operational and the audio mixer 20 has received an individual alarm signal from one or more of the computers 16a-16n, the fault detection algorithm 32 may be configured to trigger a universal alarm using one of the conventional speakers 40a-40n as will be described in detail hereinafter. The fault detection algorithm 32 configured in the manner described provides a backup system to ensure the alarm is heard by an appropriate technician even if the directional speaker 22 is not operational. According to one embodiment, the fault detection algorithm 32 is configured to verify that the directional speaker 22 is properly connected to the audio mixer 20 as a means for assessing directional speaker operational status. According to another embodiment, the fault detection algorithm 32 is configured to implement feedback from the audio sensor 24 as a means for assessing directional speaker operational status.

The directional speaker 22 is configured to receive the composite alarm signal from the audio mixer 20, and to generate a localized alarm comprising a narrow cone or beam of audible sound waves 34 directed at the technician 14a (shown in FIG. 1). The localized alarm becomes generally imperceptible to anyone outside the narrow beam of audible sound waves 34. Accordingly, a single technician can be audibly alerted to the fact that one of their patients requires attention without unnecessarily subjecting nearby technicians to the sound of the alarm. In this manner workplace noise and confusion are minimized. Additionally, by allowing the technicians 14a-14n to hear only the alarms for which they are responsible, the potential for alarm desensitization is reduced.

The computers 16a-16n respectively include an alarm trigger algorithm 36a-36n, a fault detection algorithm 38a-38n, and a conventional speaker 40a-40n. The computer 16a will now be described in more detail and in accordance with an embodiment, however, it should be appreciated that the computers 16a-16n are similarly configured such that the following disclosure applies equally to the computers 16b-16n. It should also be appreciated that, according to an alternate embodiment, a single computer operatively connected to each of the displays 18a-18n could be implemented in place of the individual computers 16a-16n.

The alarm trigger algorithm 36a of the computer 16a is configured to generate an audible alarm in order to help identify patients that require immediate attention. As an example, the alarm trigger algorithm 36a may be configured to analyze patient data from the discrete patient monitoring systems 26a-26n, and to generate an individual alarm signal based on the patient data analysis. In a non-limiting manner, the alarm trigger algorithm 36a may generate an individual alarm signal in response to patient data falling outside a predefined range, abrupt changes in patient data, the loss of a patient data signal, etc. According to an alternate embodiment, the alarm trigger algorithm 36a may be replaced by or implemented in combination with a plurality of similarly functioning algorithms disposed on each of the discrete patient monitoring systems 26a-26n. The technology embodied in the alarm trigger algorithm 36a is well known to those skilled in the art and may be implemented in a variety of different ways.

The fault detection algorithm 38a is an optional component of the computer 16a, and is configured to ensure that generated individual alarm signals from the alarm trigger algorithm 36a are effectively conveyed to the technician 14a (shown in FIG. 1) even if the directional speaker 22 in not operational. According to one embodiment, the fault detection algorithm 38a is configured to verify that the audio mixer 20 is properly connected to the computer 16a as a means for assessing directional speaker operational status. According to another embodiment, the fault detection algorithm 38a is configured to receive a signal from the audio mixer 20 as a means for assessing directional speaker operational status. If the fault detection algorithm 38a determines the directional speaker 22 is operational, the individual alarm signal is transmitted from the alarm trigger algorithm 36a to the audio mixer 20. If the fault detection algorithm 38a determines the directional speaker 22 is not operational, the individual alarm signal is transmitted from the alarm trigger algorithm 36a to the conventional speaker 40a.

The conventional speaker 40a is an optional component of the computer 16a configured to produce a universal alarm that is transmitted to and detectable by all of the technicians 14a-14n (shown in FIG. 1). It should be appreciated that conventional speaker 40a is generally implemented when there is some indication that the directional speaker 22 is not operational. According to one embodiment, the conventional speaker 40a is only implemented when the fault detection algorithm 32 and/or the fault detection algorithm 38a provide an indication that the directional speaker 22 is not operational. Although the conventional speaker 40a is shown and described as comprising an integral component of the computer 16a, it should be appreciated that the conventional speaker 40a may alternately comprise a remotely located device that is operatively connected to the computer 16a.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A centralized patient monitoring system configured to enable each of a plurality of technicians to generally simultaneously monitor multiple patients comprising:
 a plurality of computers each configured to selectively generate an individual alarm signal and adapted to receive patient data from the monitored patients;
 a display connected to the plurality of computers, said display configured to visually convey the patient data;
 a directional speaker connected to the plurality of computers, said directional speaker being configured to selectively generate a localized alarm to audibly alert one of said plurality of technicians when one of the monitored patients requires attention, wherein said localized alarm is generally imperceptible to the other of said plurality of technicians; and an audio mixer configured to receive the individual alarm signals from each of the plurality of computers, to combine the individual alarm signals into a single composite alarm signal, and to transmit the composite alarm signal to the directional speaker.

2. The centralized patient monitoring system of claim 1, wherein said localized alarm comprises a narrow beam of audible sound waves.

3. The centralized patient monitoring system of claim 1, wherein said computer includes a fault detection algorithm adapted to assess a directional speaker operational status.

4. The centralized patient monitoring system of claim 1, further comprising a conventional speaker adapted to selectively generate a universal alarm.

5. The centralized patient monitoring system of claim 1, wherein said audio mixer includes a fault detection algorithm adapted to assess a directional speaker operational status.

6. The centralized patient monitoring system of claim 1, further comprising an audio sensor adapted to assess a directional speaker operational status.

7. A centralized patient monitoring system configured to enable each of a plurality of technicians to generally simultaneously monitor multiple patients comprising:

a plurality of computers each configured to selectively generate an individual alarm signal and adapted to receive patient data from a plurality of monitored patients, and to analyze the patient data in order to identify any of said plurality of monitored patients that require attention;

a display connected to the plurality of computers, said display configured to visually convey the patient data;

a directional speaker connected to the plurality of computers, said directional speaker being configured to selectively to generate a localized alarm in response to said patient data analysis; and an audio mixer configured to receive the individual alarm signals from each of the plurality computers, to combine the individual alarm signals into a single composite alarm signal, and to transmit the composite alarm signal to the directional speaker;

wherein said localized alarm comprises a narrow beam of audible sound waves directed at one of the plurality of technicians.

8. The centralized patient monitoring system of claim 7, wherein said localized alarm is configured to audibly alert said one of the plurality of technicians, and wherein said localized alarm is configured to be generally imperceptible to the other of the plurality of technicians.

9. The centralized patient monitoring system of claim 7, wherein said computer includes a fault detection algorithm adapted to assess a directional speaker operational status.

10. The centralized patient monitoring system of claim 7, further comprising a conventional speaker adapted to selectively generate a universal alarm.

11. The centralized patient monitoring system of claim of claim 7, further comprising an audio sensor adapted to assess a directional speaker operational status.

* * * * *

UNITED STATES PATENT AND TRADEMARK OFFICE
CERTIFICATE OF CORRECTION

| | | |
|---|---|---|
| PATENT NO. | : 7,898,424 B2 | Page 1 of 1 |
| APPLICATION NO. | : 12/102432 | |
| DATED | : March 1, 2011 | |
| INVENTOR(S) | : Davis | |

It is certified that error appears in the above-identified patent and that said Letters Patent is hereby corrected as shown below:

Title Page, Item (74), under "Attorney, Agent, or Firm", delete "Adrus, Sceales, Strarke" and insert -- Andrus, Sceales, Starke --, therefor.

In Column 6, Line 8, in Claim 7, delete "plurality" and insert -- plurality of --, therefor.

In Column 6, Lines 26-27, in Claim 11, delete "of claim of claim 7," and insert -- of claim 7, --, therefor.

Signed and Sealed this
Tenth Day of May, 2011

David J. Kappos
*Director of the United States Patent and Trademark Office*